US012594403B2

(12) United States Patent
Howell

(10) Patent No.:  US 12,594,403 B2
(45) Date of Patent:      Apr. 7, 2026

(54) INTRODUCER COMPONENTS, ASSEMBLIES, AND METHODS THEREOF

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 765 days.

(21) Appl. No.: 17/894,759

(22) Filed: Aug. 24, 2022

(65) Prior Publication Data

US 2023/0064542 A1     Mar. 2, 2023

Related U.S. Application Data

(60) Provisional application No. 63/236,578, filed on Aug. 24, 2021.

(51) Int. Cl.
A61M 25/06       (2006.01)
A61M 25/00       (2006.01)

(52) U.S. Cl.
CPC .... A61M 25/0606 (2013.01); A61M 25/0097 (2013.01); A61M 25/0693 (2013.01)

(58) Field of Classification Search
CPC .......... A61M 25/0606; A61M 25/0097; A61M 25/0693
See application file for complete search history.

(56) References Cited

U.S. PATENT DOCUMENTS

| | | |
|---|---|---|
| 3,076,457 A | 2/1963 | Copen |
| 3,359,978 A | 12/1967 | Smith, Jr. |
| 4,411,654 A | 10/1983 | Boarini et al. |
| 4,743,265 A | 5/1988 | Whitehouse et al. |
| 4,886,507 A | 12/1989 | Patton et al. |
| 4,935,008 A | 6/1990 | Lewis, Jr. |

(Continued)

FOREIGN PATENT DOCUMENTS

| | | |
|---|---|---|
| CN | 106422031 B | 7/2021 |
| DE | 4136051 A1 | 7/1993 |

(Continued)

OTHER PUBLICATIONS

PCT/US2022/052884 filed Dec. 14, 2022 International Search Report and Written Opinion dated May 15, 2023.

(Continued)

*Primary Examiner* — Imani N Hayman
(74) *Attorney, Agent, or Firm* — Rutan & Tucker LLP

(57) ABSTRACT

Disclosed are introducer components, assemblies, and methods. For example, an introducer assembly can include an access guidewire loaded in a needle assembly fluidly connected to a syringe. The needle assembly can include a needle and a valve thereover. The needle can include a needle shaft including a needle lumen, a needle slot in a proximal portion of the needle shaft, and a needle hub over the proximal portion of the needle shaft but proximal of the needle slot. The valve can be over the needle slot with a valve port aligned with the needle slot. The access guidewire can be loaded in the needle lumen and sealed therein by way of the valve port in a ready-to-deploy state of the introducer assembly. In this way, the access guidewire can be immediately advanced into a blood-vessel lumen of a patient upon establishing a needle tract thereto with the needle assembly.

17 Claims, 4 Drawing Sheets

(56) References Cited

U.S. PATENT DOCUMENTS

| | | |
|---|---|---|
| 4,957,489 A | 9/1990 | Cameron et al. |
| 4,994,040 A | 2/1991 | Cameron et al. |
| 5,290,244 A | 3/1994 | Moonka |
| 5,380,290 A | 1/1995 | Makower et al. |
| 5,687,727 A | 11/1997 | Kraus et al. |
| 5,735,813 A | 4/1998 | Lewis |
| 5,853,391 A | 12/1998 | Bell |
| 5,971,957 A | 10/1999 | Luther et al. |
| 6,019,736 A | 2/2000 | Avellanet et al. |
| 6,159,195 A | 12/2000 | Ha et al. |
| 7,172,587 B2 | 2/2007 | Poole et al. |
| 7,938,820 B2 | 5/2011 | Webster et al. |
| 8,882,713 B1 | 11/2014 | Call et al. |
| 2002/0072712 A1 | 6/2002 | Nool et al. |
| 2003/0205843 A1 | 11/2003 | Adams |
| 2004/0092879 A1 | 5/2004 | Kraus et al. |
| 2004/0236346 A1 | 11/2004 | Parker |
| 2005/0021124 A1 | 1/2005 | Cunniffe et al. |
| 2005/0043684 A1 | 2/2005 | Basta et al. |
| 2007/0276288 A1 | 11/2007 | Khaw |
| 2008/0009793 A1 | 1/2008 | Dabbs |
| 2008/0027380 A1 | 1/2008 | Wholey et al. |
| 2008/0091137 A1 | 4/2008 | Reavill |
| 2009/0187147 A1 | 7/2009 | Kurth et al. |
| 2011/0071502 A1 | 3/2011 | Asai |
| 2013/0184659 A1 | 7/2013 | Byrnes et al. |
| 2015/0224287 A1 | 8/2015 | Bian et al. |
| 2015/0320968 A1 | 11/2015 | Konstantino et al. |
| 2016/0175563 A1 | 6/2016 | Woehr et al. |
| 2016/0220786 A1 | 8/2016 | Mitchell et al. |
| 2016/0310704 A1 | 10/2016 | Ng et al. |
| 2017/0035996 A1 | 2/2017 | O'Fallon |
| 2017/0258489 A1 | 9/2017 | Galili et al. |
| 2017/0296792 A1 | 10/2017 | Ornelas Vargas et al. |
| 2018/0043138 A1 | 2/2018 | Chu |
| 2019/0015637 A1 | 1/2019 | Jacobs |
| 2019/0022353 A1 | 1/2019 | Khanicheh et al. |
| 2019/0038113 A1 | 2/2019 | Chu |
| 2019/0134374 A1 | 5/2019 | Korkuch et al. |
| 2020/0008838 A1 | 1/2020 | Frey et al. |
| 2020/0107859 A1 | 4/2020 | Zhu |
| 2020/0147349 A1 | 5/2020 | Holt |
| 2020/0170559 A1 | 6/2020 | Burkholz et al. |
| 2020/0188650 A1 | 6/2020 | Al-Ali |
| 2020/0197682 A1 | 6/2020 | Franklin et al. |
| 2021/0085927 A1 | 3/2021 | Howell |
| 2021/0121661 A1 | 4/2021 | Howell |
| 2021/0330941 A1 | 10/2021 | Howell et al. |
| 2021/0332274 A1 | 10/2021 | Hoshi et al. |
| 2021/0361915 A1 | 11/2021 | Howell et al. |
| 2021/0402153 A1 | 12/2021 | Howell et al. |
| 2022/0362524 A1 | 11/2022 | Howell |
| 2022/0370762 A1 | 11/2022 | Blanchard et al. |
| 2023/0039733 A1 | 2/2023 | Howell |
| 2023/0041261 A1 | 2/2023 | Howell |
| 2023/0043989 A1 | 2/2023 | Howell |
| 2023/0086639 A1 | 3/2023 | Howell |
| 2023/0096377 A1 | 3/2023 | West et al. |
| 2023/0149667 A1 | 5/2023 | Lindekugel et al. |
| 2023/0181878 A1 | 6/2023 | Blanchard et al. |
| 2023/0201537 A1 | 6/2023 | Howell et al. |
| 2023/0201538 A1 | 6/2023 | Howell et al. |
| 2023/0218867 A1 | 7/2023 | Howell et al. |
| 2023/0381481 A1 | 11/2023 | Pizzato |
| 2024/0082549 A1 | 3/2024 | Spataro et al. |
| 2024/0226507 A1 | 7/2024 | Spataro |
| 2025/0375594 A1 | 12/2025 | Lindekugel |
| 2026/0021276 A1 | 1/2026 | Blanchard et al. |

FOREIGN PATENT DOCUMENTS

| | | |
|---|---|---|
| DE | 19750090 A1 | 6/1999 |
| EP | 0067260 A1 | 12/1982 |
| EP | 0155331 A1 | 9/1985 |
| EP | 0499147 A2 | 8/1992 |
| EP | 0641571 A1 | 3/1995 |
| EP | 1338299 A1 | 8/2003 |
| EP | 3193813 A1 | 7/2017 |
| EP | 3473291 A1 | 4/2019 |
| JP | H02255156 A | 10/1990 |
| JP | H077971 Y2 | 3/1995 |
| JP | 2004254879 A | 9/2004 |
| JP | 2009232917 A | 10/2009 |
| JP | 5101359 B2 | 12/2012 |
| WO | 8906986 A1 | 8/1989 |
| WO | 95/09662 A1 | 4/1995 |
| WO | 98/10821 A1 | 3/1998 |
| WO | 99/59651 A2 | 11/1999 |
| WO | 02/078776 A2 | 10/2002 |
| WO | 2005096778 A2 | 10/2005 |
| WO | 2009094089 A1 | 7/2009 |
| WO | 2011143621 A1 | 11/2011 |
| WO | 2012101089 A1 | 8/2012 |
| WO | 2013064215 A1 | 5/2013 |
| WO | 2015/061172 A1 | 4/2015 |
| WO | 2016042544 A1 | 3/2016 |
| WO | 2016123278 A1 | 8/2016 |
| WO | 2016187063 A1 | 11/2016 |
| WO | 2020206280 A2 | 10/2020 |
| WO | 2021216902 A1 | 10/2021 |
| WO | 2021222116 A2 | 11/2021 |
| WO | 2022/204049 A1 | 9/2022 |
| WO | 2022/246271 A2 | 11/2022 |
| WO | 2022/245774 A3 | 12/2022 |
| WO | 2023014994 A1 | 2/2023 |
| WO | 2023018669 A1 | 2/2023 |
| WO | 2023018729 A1 | 2/2023 |
| WO | 2023018733 A1 | 2/2023 |
| WO | 2023028138 A2 | 3/2023 |
| WO | 2023049174 A1 | 3/2023 |
| WO | 2023091586 A1 | 5/2023 |
| WO | 2023114324 A1 | 6/2023 |
| WO | 2023122312 A1 | 6/2023 |
| WO | 2023129457 A1 | 7/2023 |
| WO | 2023137077 A1 | 7/2023 |
| WO | 2024059073 A1 | 3/2024 |
| WO | 2024151869 A1 | 7/2024 |
| WO | 2025259604 A1 | 12/2025 |

OTHER PUBLICATIONS

PCT/US2022/053724 filed Dec. 21, 2022 International Search Report and Written Opinion dated May 10, 2023.

PCT/US2023/010623 filed Jan. 11, 2023, International Search Report and Written Opinion dated Jul. 6, 2023.

PCT/US2022/039742 filed Aug. 8, 2022 International Preliminary Report on Patentability dated Feb. 13, 2024.

PCT/US2022/041368 filed Aug. 24, 2022 International Preliminary Report on Patentability dated Feb. 27, 2024.

PCT/US2022/044242 filed Sep. 21, 2022 International Preliminary Report on Patentability dated Mar. 26, 2024.

PCT/US2022/053887 filed Dec. 22, 2022 International Search Report and Written Opinion dated May 8, 2023.

PCT/US2023/032545 filed Sep. 12, 2023 International Search Report and Written Opinion dated Feb. 13, 2024.

U.S. Appl. No. 17/700,152, filed Mar. 21, 2022 Restriction Requirement dated Jan. 31, 2025.

U.S. Appl. No. 17/746,113, filed May 17, 2022 Restriction Requirement dated Dec. 11, 2024.

U.S. Appl. No. 17/750,097, filed May 20, 2022 Restriction Requirement dated Mar. 20, 2025.

U.S. Appl. No. 17/884,307, filed Aug. 9, 2022 Non-Final Office Action dated Apr. 2, 2025.

PCT/US2022/021187 filed Mar. 21, 2022 International Search Report and Written Opinion dated Jun. 17, 2022.

PCT/US2022/030365 filed May 20, 2022 International Search Report and Written Opinion dated Apr. 4, 2023.

PCT/US2022/041368 filed Aug. 24, 2022 International Search Report and Written Opinion dated Mar. 21, 2023.

PCT/US2022/044242 filed Sep. 21, 2022 International Search Report and Written Opinion dated Feb. 8, 2023.

(56)                    References Cited

OTHER PUBLICATIONS

PCT/US2022/050280 filed Nov. 17, 2022 International Search Report and Written Opinion dated Apr. 17, 2023.
PCT/US2022/029561 filed May 17, 2022 International Search Report and Written Opinion dated Nov. 9, 2022.
PCT/US2022/039742 filed Aug. 8, 2022 International Search Report and Written Opinion dated Dec. 21, 2022.
PCT/US2022/039852 filed Aug. 9, 2022 International Search Report and Written Opinion dated Dec. 6, 2022.
PCT/US2022/039861 filed Aug. 9, 2022, International Search Report and Written Opinion dated Jan. 5, 2023.
Adam et al. (Gastrointestinal Endoscopy vol. 77, No. 5S 2013, 1020) (Year: 2010).
Lapalu et al. "Totally implantable port management: impact of positive pressure during needle withdrawal on catheter tip occlusion (an experimental study)" The Journal of Vascular Access 2010; 11: 46-51, 2010 Wichtig Editore, Original Article, 2010.
PCT/US2024/011269 filed Jan. 11, 2024 International Search Report and Written Opinion dated May 15, 2024.
U.S. Appl. No. 17/700,152, filed Mar. 21, 2022 Non-Final Office Action dated Aug. 14, 2025.
U.S. Appl. No. 17/700,152, filed Mar. 21, 2022 Restriction Requirement dated Apr. 29, 2025.
U.S. Appl. No. 17/746,113, filed May 17, 2022 Non-Final Office Action dated Apr. 7, 2025.
U.S. Appl. No. 17/750,097, filed May 20, 2022 Notice of Allowance dated Jun. 27, 2025.
U.S. Appl. No. 17/883,490, filed Aug. 8, 2022 Non-Final Office Action dated Jul. 31, 2025.
U.S. Appl. No. 17/884,402, filed Aug. 9, 2022 Non-Final Office Action dated May 30, 2025.
U.S. Appl. No. 17/884,402, filed Aug. 9, 2022 Notice of Allowance dated Sep. 10, 2025.
U.S. Appl. No. 17/949,734, filed Sep. 21, 2022 Non-Final Office Action dated Aug. 4, 2025.
U.S. Appl. No. 17/989,325, filed Nov. 17, 2022 Restriction Requirement dated Aug. 28, 2025.
U.S. Appl. No. 18/081,491, filed Dec. 14, 2022 Non-Final Office Action dated Aug. 22, 2025.
PCT/US2025/032881 filed Jun. 9, 2025 International Search Report and Written Opinion dated Sep. 24, 2025.
U.S. Appl. No. 17/884,307, filed Aug. 9, 2022 Final Office Action dated Oct. 23, 2025.
U.S. Appl. No. 18/086,517, filed Dec. 21, 2022 Non-Final Office Action dated Oct. 31, 2025.
U.S. Appl. No. 18/087,676, filed Dec. 22, 2022 Restriction Requirement dated Oct. 8, 2025.
U.S. Appl. No. 18/095,968, filed Jan. 11, 2023 Restriction Requirement dated Nov. 24, 2025.
U.S. Appl. No. 17/700,152, filed Mar. 21, 2022 Final Office Action dated Feb. 12, 2026.
U.S. Appl. No. 17/883,490, filed Aug. 8, 2022 Final Office Action dated Dec. 22, 2025.
U.S. Appl. No. 17/949,734, filed Sep. 21, 2022 Final Office Action dated Feb. 5, 2026.
U.S. Appl. No. 17/989,325, filed Nov. 17, 2022 Notice of Allowance dated Jan. 22, 2026.
U.S. Appl. No. 18/081,491, filed Dec. 14, 2022 Final Office Action dated Jan. 12, 2026.

INTRODUCER COMPONENTS, ASSEMBLIES, AND METHODS THEREOF

PRIORITY

This application claims the benefit of priority to U.S. Provisional Patent Application No. 63/236,578, filed Aug. 24, 2021, which is incorporated by reference in its entirety into this application.

BACKGROUND

A guidewire is typically placed in a blood vessel with an introducer assembly before inserting a central venous catheter ("CVC") or the like into the blood vessel over the guidewire. The introducer assembly typically includes a needle connected to a syringe. Upon accessing the blood vessel with the needle, the needle must be disconnected from the syringe to allow insertion of the guidewire into the needle through a needle hub thereof and, subsequently, into the blood vessel. Disconnecting the needle from the syringe as well as inserting the guidewire into the needle risk puncturing a backwall of the blood vessel, losing access to the blood vessel, or both due to overhandling the needle. What is needed is an introducer assembly that does not require disconnecting the needle from the syringe for inserting the guidewire into the blood vessel.

Disclosed herein are introducer components, assemblies, and methods that address the foregoing.

SUMMARY

Disclosed herein is an introducer assembly including, in some embodiments, a vacuum-generating device, a needle assembly fluidly connected to the vacuum-generating device, and an access guidewire loaded in the needle assembly. The needle assembly includes a needle and a valve over the needle. The needle includes a needle shaft including a needle lumen, a needle slot in a proximal portion of the needle shaft, and a needle hub over the proximal portion of the needle shaft but proximal of the needle slot. The valve is over the needle slot. The valve includes a valve port aligned with the needle slot. The access guidewire is loaded in the needle lumen and sealed therein by way of the valve port in a ready-to-deploy state of the introducer assembly.

In some embodiments, the valve includes an elastomeric sleeve.

In some embodiments, the elastomeric sleeve is adhered to the needle shaft over the needle slot.

In some embodiments, the valve port includes a hole in the elastomeric sleeve aligned with the needle slot. The hole has an inner diameter smaller than the outer diameter of the access guidewire.

In some embodiments, the valve port includes a slit in the elastomeric sleeve. The slit is aligned with the needle slot.

In some embodiments, the valve port includes a plurality of intersecting slits in the elastomeric sleeve. The intersecting slits are aligned with the needle slot.

In some embodiments, the valve further includes a rigid housing over the elastomeric sleeve.

In some embodiments, the valve port further includes a through hole in the rigid housing. The through hole in the rigid sleeve is aligned with the needle slot.

In some embodiments, the valve port further includes an 'O'-ring disposed in the through hole. The 'O'-ring has an inner diameter smaller than the outer diameter of the access guidewire.

In some embodiments, the access guidewire includes a 'J'-shaped guidewire tip that assumes a straightened state in the ready-to-deploy state of the introducer assembly. In addition, the guidewire tip assumes a curved state when the guidewire tip is advanced beyond a distal end of the needle shaft in a deployed state of the introducer assembly.

In some embodiments, the access guidewire includes a bare-wire portion and a wound-wire portion proximal of the bare-wire portion. The bare-wire portion distally extends through the valve port in at least the ready-to-deploy state of the introducer assembly.

In some embodiments, the access guidewire includes a proximal portion proximally extending from the valve port in the ready-to-deploy state of the introducer assembly. The proximal portion of the access guidewire is disposed in a sterile barrier configured to maintain sterility of the access guidewire.

In some embodiments, the needle hub further include a needle-hub connector. The needle-hub connector includes a needle-hub bore in a proximal portion of the needle hub. A syringe tip of a syringe as the vacuum-generating device is disposed in the needle-hub bore, thereby fluidly connecting the needle assembly to the vacuum-generating device in the ready-to-deploy state of the introducer assembly.

Also disclosed herein is a needle assembly including, in some embodiments, a needle and a valve over the needle. The needle includes a needle shaft including a needle lumen, a needle slot in a proximal portion of the needle shaft, and a needle hub over the proximal portion of the needle shaft but proximal of the needle slot. The valve includes an elastomeric sleeve over the needle slot. The valve includes a valve port aligned with the needle slot.

In some embodiments, the elastomeric sleeve is adhered to the needle shaft over the needle slot.

In some embodiments, the valve port includes a slit in the elastomeric sleeve. The slit is aligned with the needle slot.

In some embodiments, the valve port includes a plurality of intersecting slits in the elastomeric sleeve. The intersecting slits are aligned with the needle slot.

In some embodiments, the valve further includes a rigid housing over the elastomeric sleeve.

In some embodiments, the valve port further includes a through hole in the rigid housing. The through hole in the rigid sleeve is aligned with the needle slot.

In some embodiments, the needle hub further includes a needle-hub connector. The needle-hub connector includes a needle-hub bore in a proximal portion of the needle hub. The needle-hub bore is configured to accept a syringe tip of a syringe inserted therein for fluidly connecting the needle assembly to the syringe.

Also disclosed herein is a method for securing vascular access. The method includes, in some embodiments, an introducer assembly-obtaining step, a needle tract-establishing step, and an access guidewire-advancing step. The introducer assembly-obtaining step includes obtaining an introducer assembly. The introducer assembly includes a syringe, a needle assembly fluidly connected to the syringe, and an access guidewire loaded in the needle assembly. The needle assembly includes a needle slot in a proximal portion of a needle shaft and a valve over the needle slot. The valve is distal of a needle hub over the proximal portion of the needle shaft. The access guidewire is loaded in a needle lumen of the needle shaft and sealed therein by way of a valve port of the valve. The needle tract-establishing step includes establishing a needle tract from an area of skin to a blood-vessel lumen of a patient with the needle assembly. The access guidewire-advancing step includes advancing at least a guidewire tip of the access guidewire into the blood-vessel lumen for the securing of the vascular access.

In some embodiments, the method further includes an introducer assembly-adjusting step. The introducer assembly-adjusting step includes adjusting the introducer assembly such that the introducer assembly is in a ready-to-deploy state thereof. In the ready-to-deploy state of the introducer assembly, the guidewire tip of the access guidewire is just proximal of a needle tip in a distal portion of the needle shaft. This enable the advancing of the access guidewire into the blood-vessel lumen in accordance with the access guidewire-advancing step immediately upon the establishing of the needle tract in the needle tract-establishing step.

In some embodiments, the access guidewire-advancing step includes grabbing the access guidewire with a thumb and one or more fingers of a hand and pushing the access guidewire through the valve port and into the needle slot.

In some embodiments, the valve includes an elastomeric sleeve. In addition, the valve port includes one or more slits in the elastomeric sleeve aligned with the needle slot.

In some embodiments, the valve further includes a rigid housing over the elastomeric sleeve. In addition, the valve port further includes a through hole in the rigid housing aligned with the needle slot.

In some embodiments, the access guidewire-advancing step allows the guidewire tip of the access guidewire to transition from a straightened state in the needle shaft to a curved state in the blood-vessel lumen.

In some embodiments, the method of further includes a plunger-withdrawing step. The plunger-withdrawing step includes withdrawing a plunger from a barrel of the syringe to create a slight vacuum before reaching the blood-vessel lumen in the needle tract-establishing step. The slight vacuum ensures blood flashes back into at least a syringe tip to confirm the establishing of the needle tract in the needle tract-establishing step.

In some embodiments, the method further includes a blood-aspirating step. The blood-aspirating step includes aspirating blood with the syringe to confirm the establishing of the needle tract in the needle tract-establishing step. The valve port forms a fluid-tight seal around a bare-wire portion of the access guidewire for maintaining a vacuum during the blood-aspirating step.

In some embodiments, the method further includes a needle assembly-withdrawing step. The needle assembly-withdrawing step includes withdrawing the needle assembly from the patient leaving the access guidewire in the blood-vessel lumen. The withdrawing of the needle assembly from the patient includes withdrawing the needle assembly over a proximal portion of the access guidewire until a proximal end of the access guidewire escapes from the needle shaft.

In some embodiments, the needle assembly-withdrawing step includes holding the access guidewire in place at or near the area of skin including the needle tract during the withdrawing of the needle assembly over the proximal portion of the access guidewire.

In some embodiments, the method further includes an introducer assembly-disconnecting step. The introducer assembly-disconnecting step includes disconnecting the needle assembly from the syringe before the needle assembly-withdrawing step.

In some embodiments, the method further an air-bleeding step. The air-bleeding step includes bleeding air into the valve port while withdrawing the needle assembly from the patient in the needle assembly-withdrawing step. The air-bleeding step includes pushing the access guidewire to a side of the valve port. The bleeding of air into the valve port obviates disconnecting the needle assembly from the syringe as in the introducer assembly-disconnecting step.

These and other features of the concepts provided herein will become more apparent to those of skill in the art in view of the accompanying drawings and following description, which describe particular embodiments of such concepts in greater detail.

DRAWINGS

DESCRIPTION

Figure 1:
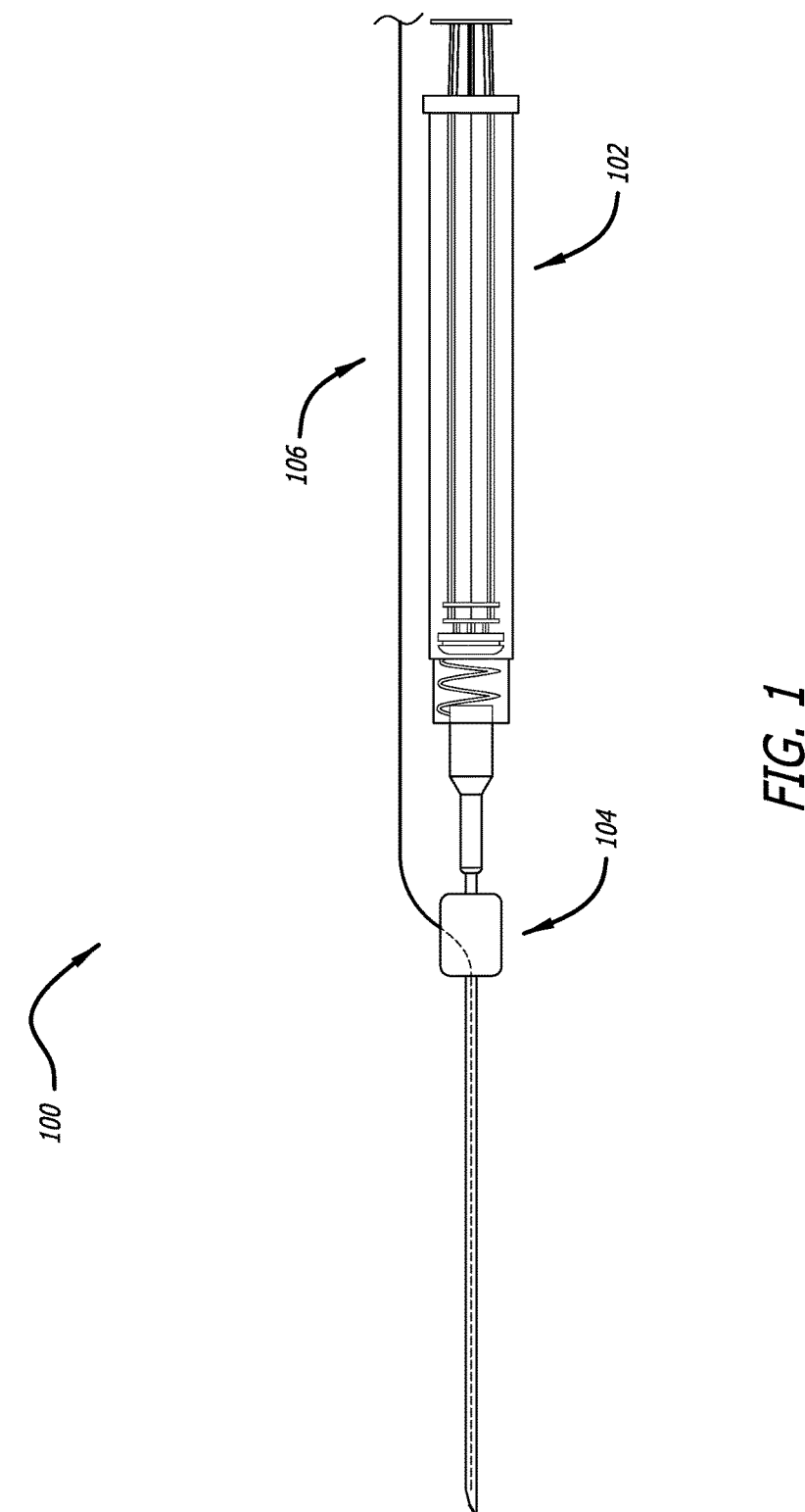
FIG. 1 illustrates a side view of an introducer assembly in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, a guidewire is typically placed in a blood vessel with an introducer assembly before inserting a CVC or the like into the blood vessel over the guidewire. The introducer assembly typically includes a needle connected to a syringe. Upon accessing the blood vessel with the needle, the needle must be disconnected from the syringe to allow insertion of the guidewire into the needle through a needle hub thereof and, subsequently, into the blood vessel. Disconnecting the needle from the syringe as well as inserting the guidewire into the needle risk puncturing a backwall of the blood vessel, losing access to the blood vessel, or both due to overhandling the needle. What is needed is an introducer assembly that does not require disconnecting the needle from the syringe for inserting the guidewire into the blood vessel.

Disclosed herein are introducer components, assemblies, and methods that do not require disconnecting the needle from the syringe or any other vacuum-generating device for inserting the guidewire into a blood vessel like typical introducer assemblies. Such introducer components, assemblies, and methods are advantageous in that they do not have the same risk of puncturing a backwall of the blood vessel or losing access to the blood vessel due to overhandling. In an example, an introducer assembly is disclosed that includes an access guidewire loaded in a needle assembly fluidly connected to a vacuum-generating device. The needle assembly includes a needle and a valve thereover. The needle includes a needle shaft including a needle lumen, a needle slot in a proximal portion of the needle shaft, and a needle hub over the proximal portion of the needle shaft but proximal of the needle slot. The valve is over the needle slot with a valve port aligned with the needle slot. The access guidewire is loaded in the needle lumen and sealed therein by way of the valve port in a ready-to-deploy state of the introducer assembly. In this way, the access guidewire can be immediately advanced into a blood-vessel lumen of a patient upon establishing a needle tract thereto with the needle assembly. In another example, a method is disclosed for securing vascular access with the foregoing introducer assembly. Again, these and other features will become more apparent in view of the accompanying drawings and following description, which describe particular embodiments in greater detail.

Introducer Assemblies

Figure 2:
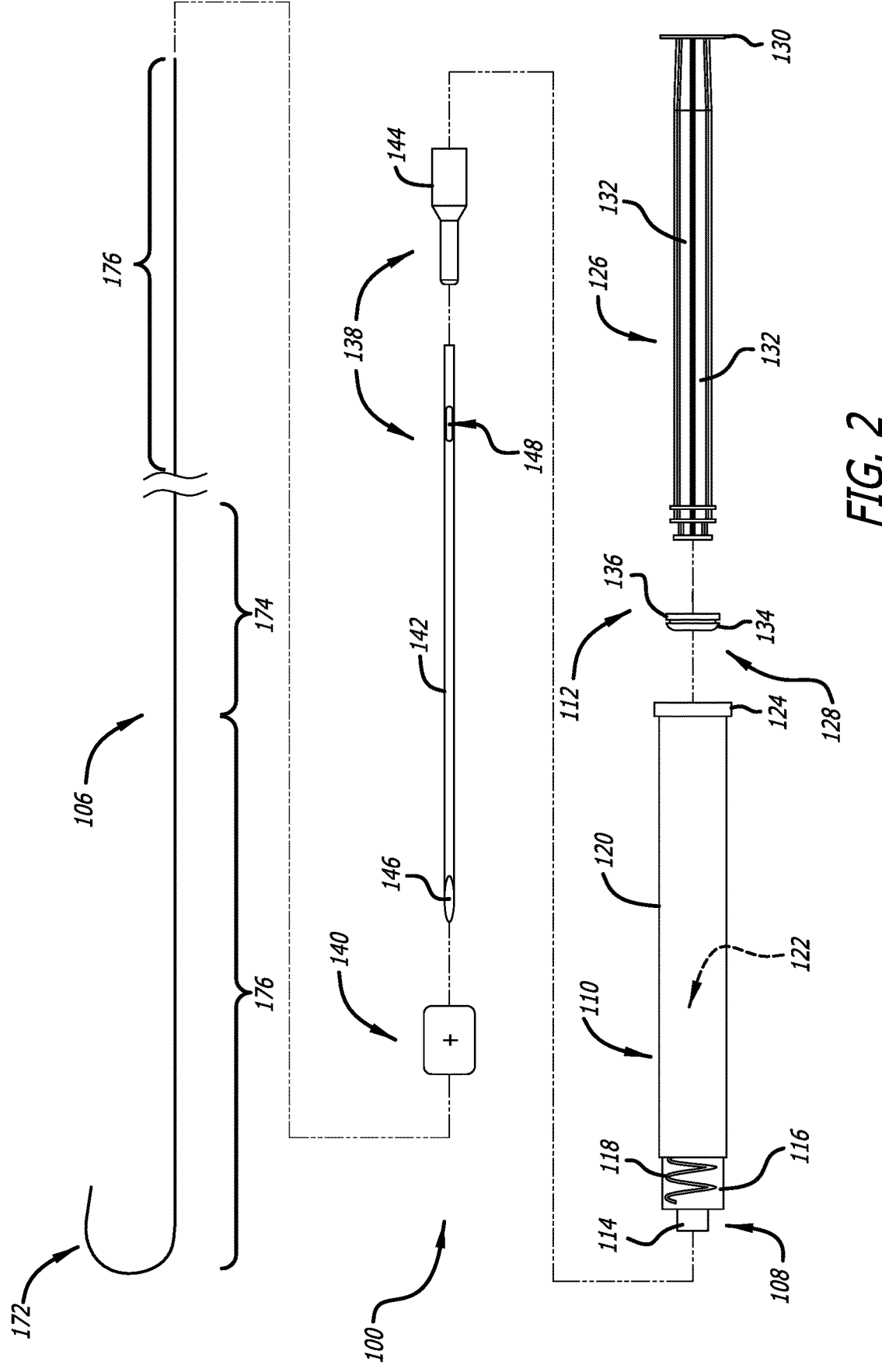
FIG. 2 illustrates an exploded view of the introducer assembly in accordance with some embodiments.

FIGS. 1 and 2 illustrate different views of an introducer assembly 100 in accordance with some embodiments.

As shown, the introducer assembly 100 includes a syringe 102 for a vacuum-generating device and a needle assembly 104 fluidly connected to the syringe 102 in a ready-to-deploy state of the introducer assembly 100. In addition, the introducer assembly 100 can include an access guidewire 106 loaded in the needle assembly 104 in the ready-to-deploy state of the introducer assembly 100. As set forth below, the access guidewire 106 is loaded in the needle lumen 152 and sealed therein by way of the valve port 166 in such a ready-to-deploy state of the introducer assembly 100. In addition, the guidewire tip 172 of the access guidewire 106 advantageously extends into the needle lumen 152 just proximal of the needle tip 146. In this way, the access guidewire 106 is available to be immediately and directly advanced into a blood-vessel lumen of a patient upon establishing a needle tract thereto with the needle 138.

The syringe 102 includes a syringe hub 108, a barrel 110, and a plunger 112 disposed in the barrel 110 in at least the ready-to-deploy state of the introducer assembly 100.

The syringe hub 108 includes a syringe tip 114 extending from a distal portion (e.g., a distal end) of the barrel 110. In addition, the syringe hub 108 can include a threaded collar 116 extending from the distal portion (e.g., the distal end) of the barrel 110 around the syringe tip 114.

The syringe tip 114 is configured to insert into the needle-hub bore 160 of the needle hub-connector of the needle hub 144 for fluidly connecting the syringe 102 to the needle assembly 104. Indeed, the syringe tip 114 can have a Luer taper (e.g., a 6% taper) configured to insert into the needle-hub bore 160, which needle-hub bore 160 is complementarily configured as set forth below.

The threaded collar 116 includes internal threads 118 configured to screw together with the optional needle-hub flange of the needle hub 144 set forth below. When present, the threaded collar 116 of the syringe hub 108 advantageously provides a so-called Luer lock-style connection with the needle-hub flange of the needle hub 144 for added security against inadvertent disconnection over that provided by an otherwise Luer slip-style connection.

The barrel 110 includes a barrel wall 120, a barrel chamber 122 defined by the barrel wall 120, and a barrel flange 124, barrel collar, or the like outwardly extending from a proximal portion (e.g., a proximal end) of the barrel 110 or barrel wall 120 configured for actuating the syringe 102 together with the plunger flange 130, the plunger collar, or the like set forth below.

The barrel chamber 122 is configured to accept the plunger 112 when inserted therein. Indeed, the barrel chamber 122 extends from a distal end of the barrel 110, which is a closed end of the barrel 110 (excepting the syringe tip 114), to the proximal end of the barrel 110, which is an open end of the barrel 110 into which the plunger 112 can be inserted.

The plunger 112 includes a one-piece plunger shaft 126, a piston 128 fitted over a distal portion (e.g., a distal end) of the plunger shaft 126, and a plunger flange 130, a plunger collar, or the like outwardly extending from a proximal portion (e.g., a proximal end) of the plunger 112 configured for actuating the syringe 102 together with the barrel flange 124, barrel collar, or the like.

The plunger shaft 126 can include orthogonal struts 132 meeting along their longitudinal edges at a central axis of the plunger shaft 126. However, the plunger shaft 126 can take other forms, so the plunger shaft 126 is not limited to the orthogonal struts 132.

The piston 128, which can be an integral, elastomeric piston, includes one or more rings configured to respectively form one or more seals with the barrel wall 120. The one-or-more rings include at least a leading ring 134 configured to form a seal with the barrel wall 120. The one-or-more rings can also include a trailing ring 136 as shown in FIG. 2. Like the leading ring 134, the trailing ring 136 is configured to form a seal with the barrel wall 120. Indeed, the trailing ring 136, when present, provides a backup seal with the barrel wall 120. Together, the leading ring 134 and the trailing ring 136 ensure the seal (e.g., the seal provided by the leading ring 134, the trailing ring 136, or both the leading ring 134 and the trailing ring 136) between the piston 128 and the barrel wall 120 remains intact while the syringe 102 is actuated, thereby allowing the syringe 102 to consistently aspirate a liquid such as blood when the plunger 112 is withdrawn from the barrel 110.

Figures 3, 4:
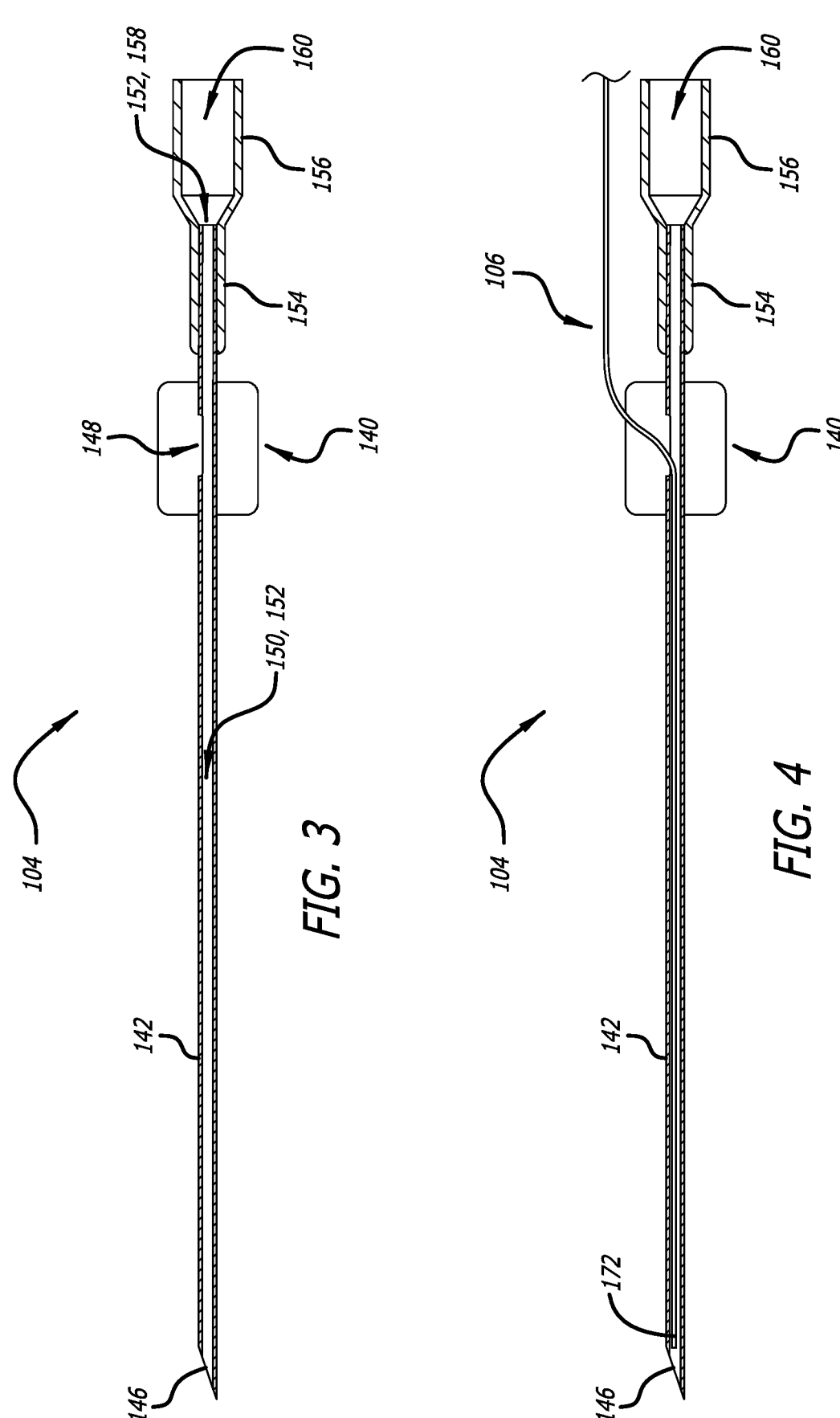
FIG. 3 illustrates a longitudinal cross section of the needle assembly in accordance with some embodiments.
FIG. 4 illustrates a longitudinal cross section of the needle assembly with an access guidewire disposed therein in accordance with some embodiments.

FIGS. 3 and 4 illustrate different views of the needle assembly 104 in accordance with some embodiments.

The needle assembly 104 includes a needle 138 and a valve 140 over the needle 138.

The needle 138 includes a needle shaft 142 and a needle hub 144 over a proximal portion of the needle shaft 142 including a proximal end of the needle shaft 142.

The needle shaft 142 includes a needle tip 146 in a distal portion of the needle shaft 142, a needle slot 148 in the proximal portion of the needle shaft 142 proximal of the needle hub 144, and a needle-shaft lumen 150 extending through an entirety of the needle shaft 142. Notably, the needle-shaft lumen 150 and the needle-hub lumen 158 set forth below together form a needle lumen 152.

The needle slot 148 is a needle through hole extending through a side of the needle shaft 142 such that the access guidewire 106 can be loaded in the needle-shaft lumen 150 or the needle lumen 152 through the needle slot 148 and sealed therein by way of the valve port 166 in the ready-to-deploy state of the introducer assembly 100. Indeed, the valve 140 is over the needle slot 148 with the valve port 166 aligned with the needle slot 148 such that the access guidewire 106 can be loaded in the needle-shaft lumen 150 or the needle lumen 152 and sealed therein by way of the valve port 166.

The needle hub 144 includes a neck 154 and a needle-hub connector 156 in a proximal portion of the needle hub 144.

The neck 154 includes a neck portion of a needle-hub lumen 158 extending through an entirety of the needle shaft 142. A remainder of the needle-hub lumen 158 is formed by the needle-hub bore 160, particularly that not occupied by the syringe tip 114 in the ready-to-deploy state of the introducer assembly 100. Notably, the needle-hub lumen 158 and the needle-shaft lumen 150 set forth above together form the needle lumen 152.

The needle-hub connector 156 includes a needle-hub bore 160 and an optional needle-hub flange about the needle-hub connector 156.

The needle-hub bore 160 is configured to accept the syringe tip 114 therein for fluidly connecting the needle assembly 104 to the syringe 102. Indeed, the needle-hub bore 160 can have a Luer taper (e.g., a 6% taper) configured to accept the syringe tip 114 therein, which syringe tip 114 is complementarily configured as set forth above.

While not shown, the optional needle-hub flange is configured to screw together with the internal threads 118 of the threaded collar 116 of the syringe hub 108. When present, the needle-hub flange advantageously provides a so-called Luer lock-style connection with the internal threads 118 of the threaded collar 116 of the syringe hub 108 for added security against inadvertent disconnection over that provided by an otherwise Luer slip-style connection.

Figure 6:
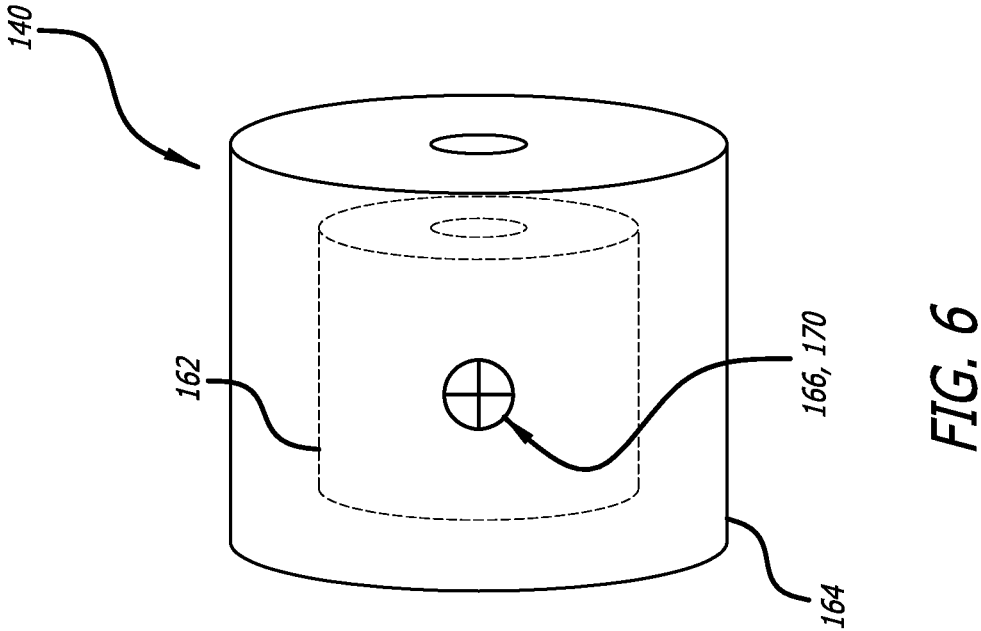
FIG. 6 illustrates another valve of the needle assembly in accordance with some embodiments.
Figure 5:
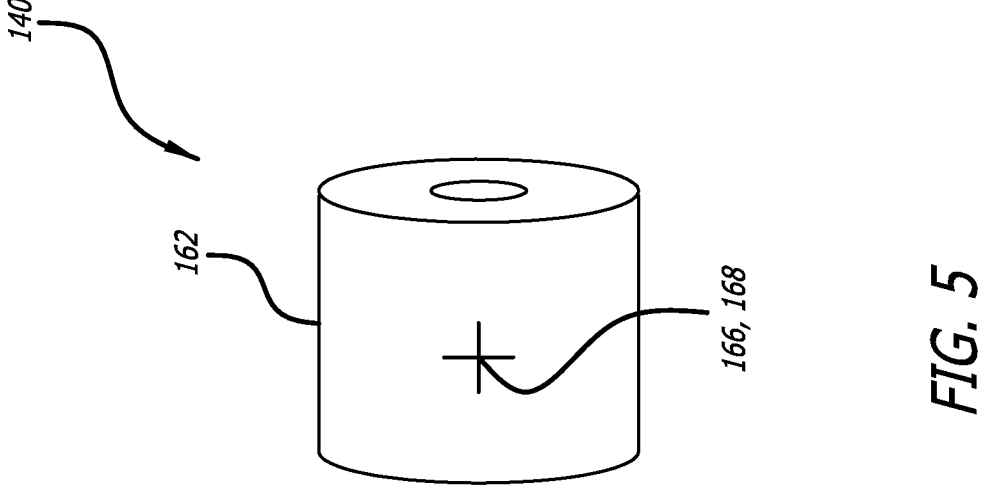
FIG. 5 illustrates a valve of the needle assembly in accordance with some embodiments.

FIGS. 5 and 6 illustrate different valves of the needle assembly 104 in accordance with some embodiments.

As shown, the valve 140 can include an elastomeric sleeve 162 and an optional rigid housing 164 over the elastomeric sleeve 162. To maintain alignment between the valve port 166 set forth below and the needle slot 148 of the needle shaft 142, the valve 140 can be adhered to the needle shaft 142. For example, the elastomeric sleeve 162 can be adhered to the needle shaft 142; however, the elastomeric sleeve 162 need not be adhered to the needle shaft 142, particularly when friction between the elastomeric sleeve 162 and the needle shaft 142 is sufficient from the fit therebetween to maintain alignment between the valve port 166 and the needle slot 148.

The valve 140 includes a valve port 166 aligned with the needle slot 148 of the needle shaft 142 under the valve 140 in the ready-to-deploy state of the introducer assembly 100. When the valve 140 includes the elastomeric sleeve 162, the valve port 166 can include a hole (e.g., a puncture hole) or one or more slits 168 in the elastomeric sleeve 162 aligned with the needle slot 148. As to the hole, the hole has an inner diameter smaller than an outer diameter of the access guidewire. As to the one-or-more slits 168, if more than one slit in the elastomeric sleeve 162 for the valve port 166, a plurality of intersecting slits is present in the elastomeric sleeve 162, wherein each slit of the intersecting slits intersects with every other slit of the intersecting slits such that an intersection of the intersecting slits is aligned with the needle slot 148. When the valve 140 includes the rigid housing 164, the valve port 166 can further include a through hole 170 in the rigid housing 164 aligned with the needle slot 148. While not shown, an 'O'-ring can be disposed in the through hole 170, wherein the 'O'-ring has an inner diameter smaller than the outer diameter of the access guidewire.

Again, the introducer assembly 100 can include the access guidewire 106 loaded in the needle assembly 104 in the ready-to-deploy state of the introducer assembly 100. The access guidewire 106 is loaded in the needle lumen 152 and sealed therein by way of the valve port 166 in such a ready-to-deploy state of the introducer assembly 100. In addition, the guidewire tip 172 of the access guidewire 106 advantageously extends into the needle lumen 152 just proximal of the needle tip 146. Because the access guidewire 106 is slidably disposed in the needle assembly 104 when present in the ready-to-deploy state of the introducer assembly 100, the access guidewire 106 is available to be immediately and directly advanced into a blood-vessel lumen of a patient upon establishing a needle tract thereto with the needle 138.

The access guidewire 106 can include a guidewire tip 172 in the form of a 'J'-shaped guidewire tip configured to prevent puncturing a back wall of a blood vessel. Such a guidewire tip assumes a straightened state in the ready-to-deploy state of the introducer assembly 100 and a curved state when the guidewire tip 172 is advanced beyond the needle tip 146 in a deployed state of the introducer assembly 100.

The access guidewire 106 can further include a bare-wire portion 174 and a wound-wire portion 176 distal of the bare-wire portion 174, proximal of the bare-wire portion 174, or both. The bare-wire portion 174 distally extends through the valve port 166 in at least the ready-to-deploy state of the introducer assembly 100 for forming a fluid-tight seal. Indeed, to maintain the fluid-tight seal even when a distal portion of the access guidewire 106 is advanced into a blood-vessel lumen, the bare-wire portion 174 can further distally extend through the valve port 166 in one-or-more deployed states of the introducer assembly 100 as well. Notably, the access guidewire 106 need not have the bare-wire portion 174 and the wound-wire portion 176. At least the foregoing bare-wire portion 174 can instead be a flat-wound or ground-wound portion of the access guidewire 106, wherein the flat-wound portion includes windings of a tape instead of a round wire, and wherein the ground-wound portion includes windings of a round wire ground down to flatten the windings.

Notably, the access guidewire 106 includes a proximal portion proximally extending from the valve port 166 in the ready-to-deploy state of the introducer assembly 100. While not shown, the proximal portion of the access guidewire 106 can be disposed in a sterile barrier (e.g., a sterile bag) configured to maintain sterility of the access guidewire 106.

Methods

Methods include at least a method for securing vascular access. Such a method includes one or more steps selected from an introducer assembly-obtaining step, an introducer assembly-adjusting step, a needle tract-establishing step, a plunger-withdrawing step, a blood-aspirating step, an access guidewire-advancing step, an introducer assembly-disconnecting step, an air-bleeding step, and a needle assembly-withdrawing step.

The introducer assembly-obtaining step includes obtaining the introducer assembly 100. As set forth above, the introducer assembly 100 includes the syringe 102, the needle assembly 104 fluidly connected to the syringe 102, and the access guidewire 106 loaded in the needle assembly 104. The needle assembly 104 includes the needle slot 148 in the proximal portion of the needle shaft 142 and the valve 140 over the needle slot 148. The valve 140 is distal of the needle hub 144 over the proximal portion of the needle shaft 142. The access guidewire 106 is loaded in the needle lumen 152 of the needle shaft 142 and sealed therein by way of the valve port 166 of the valve 140.

The introducer assembly-adjusting step includes adjusting the introducer assembly 100 such that the introducer assembly 100 is in the ready-to-deploy state thereof if not already upon performing the introducer assembly-obtaining step. Again, in the ready-to-deploy state of the introducer assembly 100, the guidewire tip 172 of the access guidewire 106 is just proximal of the needle tip 146 in the distal portion of the needle shaft 142. This enable the advancing of the access guidewire 106 into the blood-vessel lumen in accordance with the access guidewire-advancing step immediately upon the establishing of the needle tract in the needle tract-establishing step.

The needle tract-establishing step includes establishing a needle tract from an area of skin to a blood-vessel lumen of a patient with the needle 138 of the needle assembly 104.

The plunger-withdrawing step includes withdrawing the plunger 112 from the barrel 110 of the syringe 102 to create a slight vacuum before reaching the blood-vessel lumen in the needle tract-establishing step. The slight vacuum ensures blood flashes back into at least the syringe tip 114 to confirm the establishing of the needle tract in the needle tract-establishing step.

The blood-aspirating step includes aspirating blood with the syringe 102 to confirm the establishing of the needle tract in the needle tract-establishing step. The valve port 166 forms a fluid-tight seal around the bare-wire portion 174 of the access guidewire 106 for maintaining a vacuum during the blood-aspirating step.

The access guidewire-advancing step includes advancing at least the guidewire tip 172 of the access guidewire 106 into the blood-vessel lumen for the securing of the vascular access. Advancing the guidewire tip 172 into the blood-vessel lumen includes grabbing the proximal portion of the access guidewire 106 outside the introducer assembly 100 with a thumb and one or more fingers of a hand and pushing the access guidewire 106 through the valve port 166 of the valve 140 and into the needle slot 148 of the needle shaft 142. Again, the valve 140 can include the elastomeric sleeve 162 and the rigid housing 164 over the elastomeric sleeve 162 in some embodiments. In addition, the valve port 166 can include the one-or-more slits 168 in the elastomeric sleeve 162 and the through hole 170 in the rigid housing 164 thereover when the rigid housing 164 is present, wherein the valve port 166 aligned with the needle slot 148 of the needle shaft 142. The access guidewire-advancing step allows the guidewire tip 172 of the access guidewire 106 to transition from the straightened state in the needle-shaft lumen 150 of the needle shaft 142 to the curved state in the blood-vessel lumen.

The introducer assembly-disconnecting step includes disconnecting the needle assembly 104 from the syringe 102 before performing the needle assembly-withdrawing step. However, the introducer assembly-disconnecting step need not be performed if the air-bleeding step is performed.

The needle assembly-withdrawing step includes withdrawing the needle assembly 104 from the patient leaving the access guidewire 106 in the blood-vessel lumen. The withdrawing of the needle assembly 104 from the patient includes withdrawing the needle assembly 104 over the proximal portion of the access guidewire 106 until the proximal end of the access guidewire 106 escapes from the needle shaft 142. Notably, the needle assembly-withdrawing step includes holding the access guidewire 106 in place at or near the area of skin including the needle tract during the withdrawing of the needle assembly 104 over the proximal portion of the access guidewire 106.

The air-bleeding step includes bleeding air into the valve port 166 while performing the needle assembly-withdrawing step by pushing the access guidewire 106 to a side of the valve port 166; however, in some embodiments, the needle hub 144 includes a push-button bleed valve on another side of the needle hub 144 for the air-bleeding step. The bleeding of air into the valve port 166 obviates the introducer assembly-disconnecting step of disconnecting the needle assembly 104 from the syringe 102. That said, both the introducer assembly-disconnecting step and the air-bleeding step can be performed in some embodiments.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:
1. An introducer assembly, comprising:
a vacuum-generating device;
a needle assembly fluidly connected to the vacuum-generating device, the needle assembly including:

a needle including:
    a needle shaft including a needle lumen;
    a needle slot in a proximal portion of the needle
        shaft; and
    a needle hub over the proximal portion of the needle
        shaft but proximal of the needle slot; and
    a valve over the needle slot, the valve including an
        elastomeric sleeve having a valve port aligned with
        the needle slot; and
an access guidewire loaded in the needle lumen and
    sealed therein around an outer diameter of the access
    guidewire by way of the valve port in a ready-to-deploy
    state of the introducer assembly,
    wherein the access guidewire includes a 'J'-shaped
        guidewire tip that assumes a straightened state in the
        ready-to-deploy state of the introducer assembly and
        a curved state when the guidewire tip is advanced
        beyond a distal end of the needle shaft in a deployed
        state of the introducer assembly.

2. The introducer assembly of claim 1, wherein the elastomeric sleeve is adhered to the needle shaft over the needle slot.

3. The introducer assembly of claim 1, wherein the valve port includes a hole in the elastomeric sleeve aligned with the needle slot, the hole having an inner diameter smaller than the outer diameter of the access guidewire.

4. The introducer assembly of claim 1, wherein the valve port includes a slit in the elastomeric sleeve aligned with the needle slot.

5. The introducer assembly of claim 1, wherein the valve port includes a plurality of intersecting slits in the elastomeric sleeve aligned with the needle slot.

6. The introducer assembly of claim 1, wherein the valve further includes a rigid housing over the elastomeric sleeve.

7. The introducer assembly of claim 6, wherein the valve port further includes a through hole in the rigid housing aligned with the needle slot.

8. The introducer assembly of claim 7, wherein the valve port further includes an 'O'-ring disposed in the through hole having an inner diameter smaller than the outer diameter of the access guidewire.

9. The introducer assembly of claim 1, wherein the access guidewire includes a bare-wire portion and a wound-wire portion proximal of the bare-wire portion, the bare-wire portion distally extending through the valve port in at least the ready-to-deploy state of the introducer assembly.

10. The introducer assembly of claim 1, wherein the access guidewire includes a proximal portion proximally extending from the valve port in the ready-to-deploy state of the introducer assembly, the proximal portion of the access guidewire disposed in a sterile barrier configured to maintain sterility of the access guidewire.

11. The introducer assembly of claim 1, wherein the needle hub further includes a needle-hub connector including a needle-hub bore in a proximal portion of the needle hub, a syringe tip of a syringe as the vacuum-generating device disposed in the needle-hub bore, thereby fluidly connecting the needle assembly to the vacuum-generating device in the ready-to- deploy state of the introducer assembly.

12. A needle assembly, comprising:
    a needle including:
        a needle shaft including a needle lumen;
        a needle slot in a proximal portion of the needle shaft;
            and
        a needle hub over the proximal portion of the needle
            shaft but proximal of the needle slot; and
    a valve including:
    an elastomeric sleeve over the needle slot, the valve
        including a valve port aligned with the needle slot; and
    a rigid housing over the elastomeric sleeve.

13. The needle assembly of claim 12, wherein the elastomeric sleeve is adhered to the needle shaft over the needle slot.

14. The needle assembly of claim 12, wherein the valve port includes a slit in the elastomeric sleeve aligned with the needle slot.

15. The needle assembly of claim 12, wherein the valve port includes a plurality of intersecting slits in the elastomeric sleeve aligned with the needle slot.

16. The needle assembly of claim 12, wherein the valve port further includes a through hole in the rigid housing aligned with the needle slot.

17. The needle assembly of claim 12, wherein the needle hub further includes a needle-hub connector including a needle-hub bore in a proximal portion of the needle hub, the needle-hub bore configured to accept a syringe tip of a syringe inserted therein for fluidly connecting the needle assembly to the syringe.

\* \* \* \* \*